(12) United States Patent
Spenser et al.

(10) Patent No.: US 7,895,876 B2
(45) Date of Patent: Mar. 1, 2011

(54) METHOD OF CRIMPING A PROSTHETIC VALVE

(75) Inventors: Benjamin Spenser, Caesarea (IL); Netanel Benichou, Hof-Carmel (IL)

(73) Assignee: Edwards Lifesciences Corporation, Irvine, CA (US)

( * ) Notice: Subject to any disclaimer, the term of this patent is extended or adjusted under 35 U.S.C. 154(b) by 1056 days.

(21) Appl. No.: 11/544,822

(22) Filed: Oct. 5, 2006

(65) Prior Publication Data

US 2007/0061009 A1  Mar. 15, 2007

Related U.S. Application Data

(63) Continuation of application No. 11/517,881, filed on Sep. 8, 2006, now Pat. No. 7,530,253.

(60) Provisional application No. 60/716,011, filed on Sep. 9, 2005.

(51) Int. Cl.
*B21D 41/04* (2006.01)
*B21C 51/00* (2006.01)

(52) U.S. Cl. .............. 72/402; 72/482.1; 72/18.6

(58) Field of Classification Search .......... 72/402, 72/416, 452.1, 452.8, 31.06, 31.01, 18.6, 72/452.9, 482.1, 465.1, 466.8; 33/555.1–555.4
See application file for complete search history.

(56) References Cited

U.S. PATENT DOCUMENTS

| | | | |
|---|---|---|---|
| 1,438,681 A * | 12/1922 | John | 33/555.2 |
| 2,974,367 A * | 3/1961 | Doering et al. | 425/392 |
| 5,992,000 A | 11/1999 | Humphrey et al. | |
| 6,360,577 B2 | 3/2002 | Austin | |
| 6,558,418 B2 | 5/2003 | Carpentier et al. | |
| 6,629,350 B2 | 10/2003 | Motsenbocker | |
| 6,730,118 B2 * | 5/2004 | Spenser et al. | 623/1.24 |
| 6,769,161 B2 | 8/2004 | Brown et al. | |
| 6,925,847 B2 | 8/2005 | Motsenbocker | |
| 6,931,899 B2 | 8/2005 | Goff et al. | |
| 6,968,607 B2 | 11/2005 | Motsenbocker | |
| 6,988,881 B2 | 1/2006 | Motsenbocker et al. | |
| 7,010,953 B2 | 3/2006 | Stupecky | |

(Continued)

OTHER PUBLICATIONS http://www.machinesolutions.org/custom_tools_equipment/HV200.htm, 2 pages, Aug. 22, 2006.

(Continued)

*Primary Examiner* — Debra M Sullivan
(74) *Attorney, Agent, or Firm* — David L. Hauser; Guy L. Cumberbatch

(57) ABSTRACT

An improved crimping mechanism and method well-suited for use with stented prosthetic heart valves. The crimping mechanism includes a plurality of jaws configured for linear non-rotational movement toward a central axis. A rotational plate is formed with a plurality of spiral grooves or tracks for engaging the jaws. Rotational movement of the spiral tracks produces linear movement of the jaws. Nesting of the inner ends of the jaws permits each to be acted on along different radial lines while their inner faces move together evenly to reduce the crimping aperture in a smooth fashion. The crimping mechanism is particularly well-suited for use with stented prosthetic heart valves, such as a prosthetic aortic valve, though it can also be applied to other stented heart valves, venous valves, and even stent grafts which tend to be fairly large.

16 Claims, 15 Drawing Sheets

U.S. PATENT DOCUMENTS

| | | |
|---|---|---|
| 7,021,114 B2 | 4/2006 | Perreault |
| 7,069,794 B2 | 7/2006 | Motsenbocker et al. |
| 7,207,204 B2 * | 4/2007 | Weber et al. ............... 72/402 |
| 2009/0043249 A1 * | 2/2009 | Sokel ........................ 604/27 |

OTHER PUBLICATIONS http://www.machinesolutions.org/custom_tools_equipment/HV200_specs.htm, 1 page, Aug. 22, 2006.

* cited by examiner

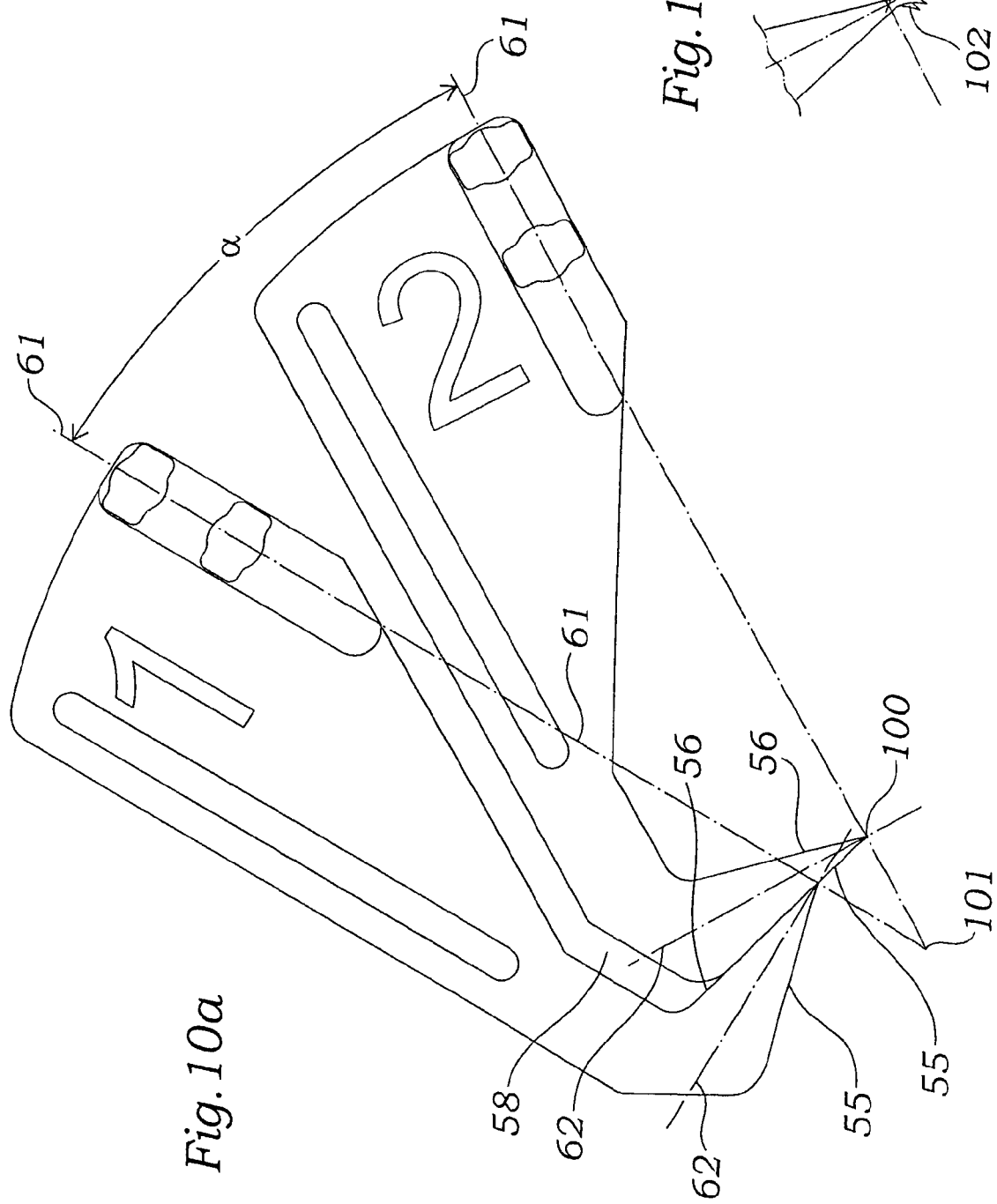

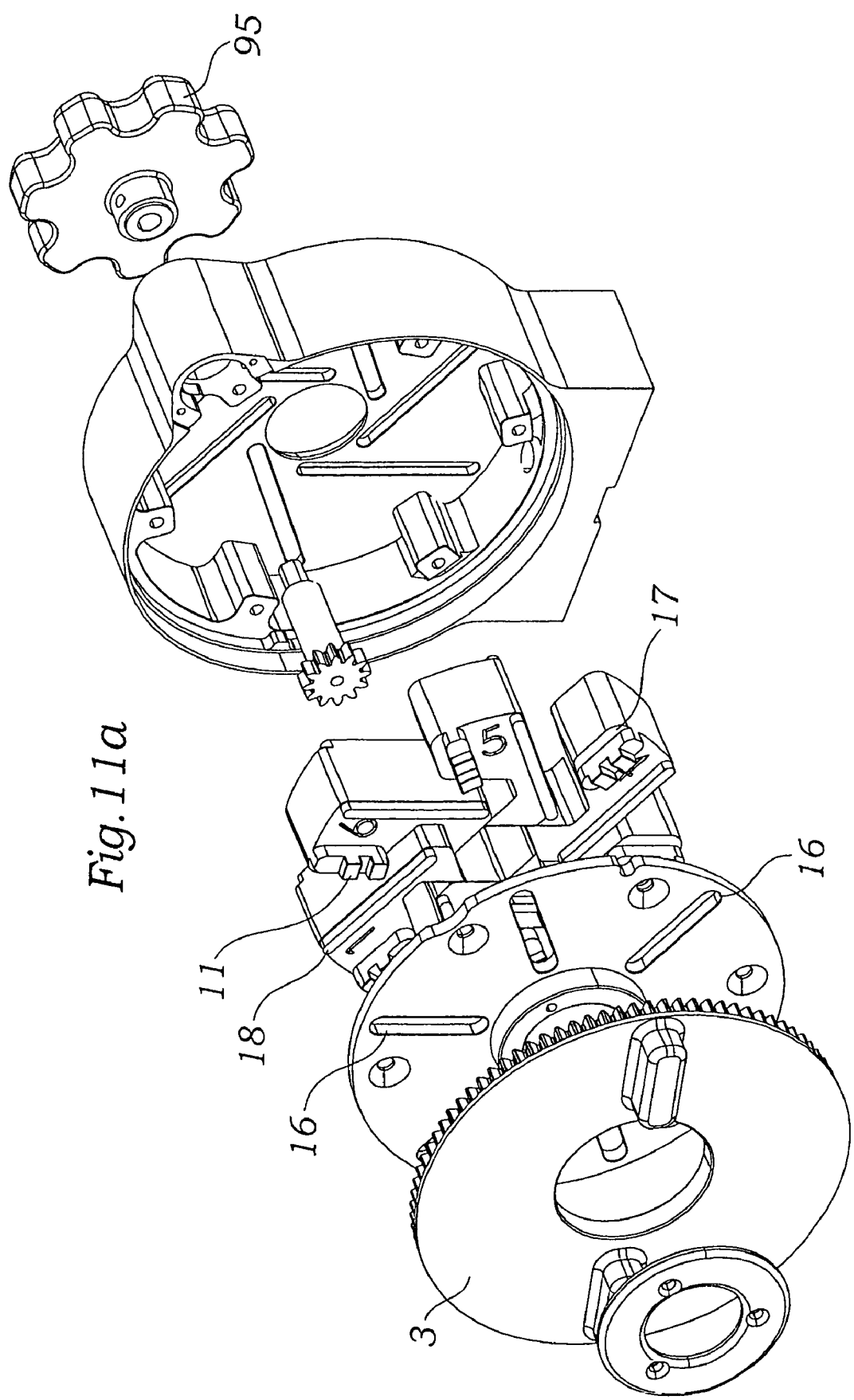

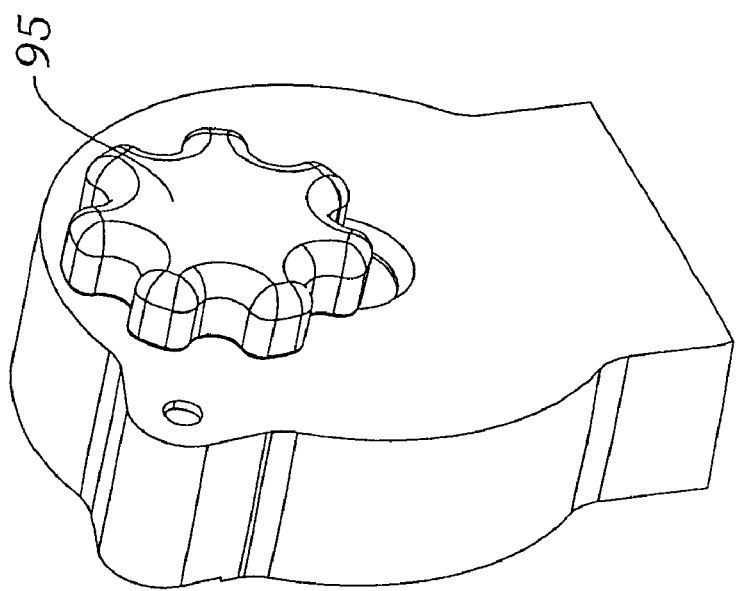
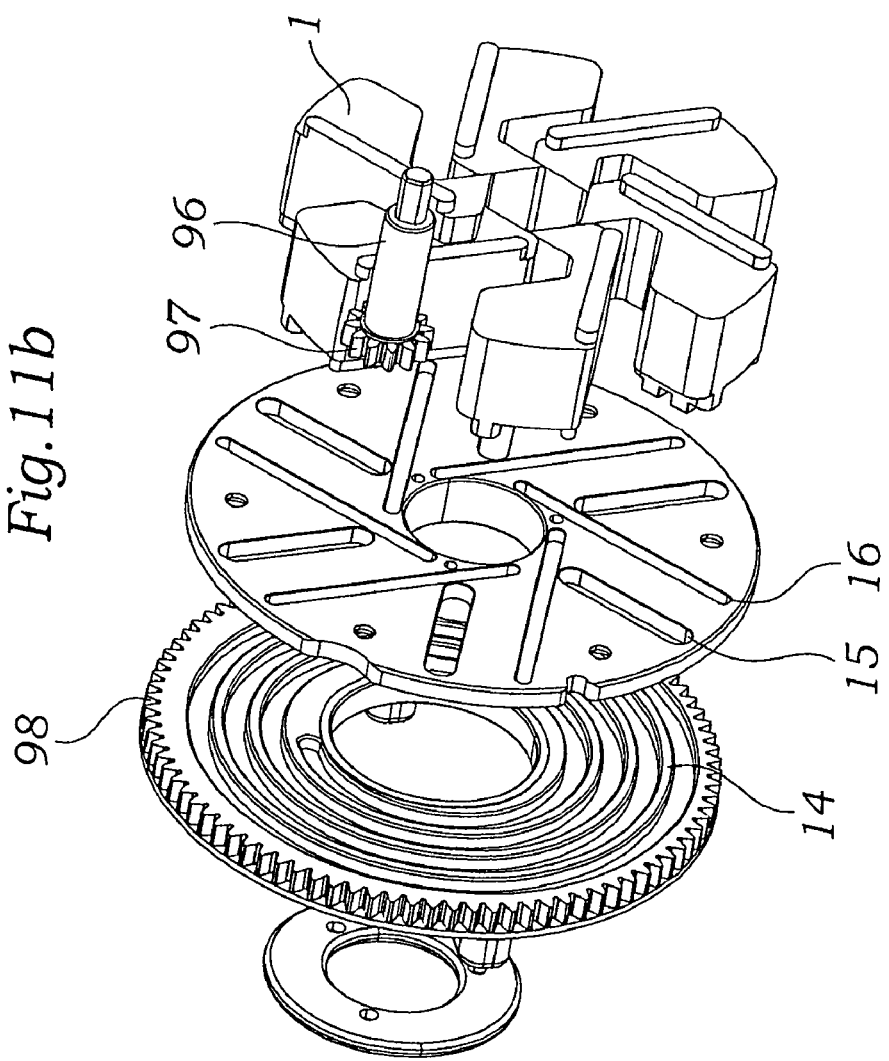
Fig. 11b

METHOD OF CRIMPING A PROSTHETIC VALVE

RELATED APPLICATION

The present application is a continuation of U.S. application Ser. No. 11/517,881, filed Sep. 8, 2006, now U.S. Pat. No. 7,530,253, which claims the benefit of priority under 35 U.S.C. §119(e) from provisional application No. 60/716,011, filed Sep. 9, 2005.

BACKGROUND OF THE INVENTION

1. Field of the Invention

The present invention relates to a crimping device and, more particularly, to a method and device for crimping a stented prosthetic valve such as a heart valve from a large diameter to a smaller diameter.

2. Description of the Related Art

A stent is a generally cylindrical prosthesis introduced into a lumen of a body vessel via a catheterization technique. Stents may be self-expanding or balloon expandable. Balloon-expandable stents are typically crimped from an initial large diameter to a smaller diameter prior to advancement to a treatment site in the body. Before crimping, a balloon expandable stent is typically placed over an expandable balloon on a catheter shaft. In cases where the stent was manufactured in its fully crimped diameter, the stent is expanded and then crimped on the balloon. To ensure safety, the crimping process should be performed in a sterile environment. Over the years, attempts have been made to crimp the stent on a balloon during the operation in the sterile field. However, most stents are now "pre-crimped" on a suitable balloon in the factory and then delivered to the physician ready for use.

One example of a crimping device based on movable segments is disclosed in U.S. Pat. No. 6,360,577 to Austin. This crimping device uses sloped planes which force jaws to move from the open position to the closed position. In one primary shortcoming associated with this type of device, the length of the sloped plane is given by a whole circle divided by the number of activated jaws. The more jaws for crimping means a shorter sloped plane for activating. The drawback of this method is the contradiction created by the equation of 360 degrees divided by the number of jaws. In order to achieve a smooth aperture for crimping the valve a large number of jaws is needed, but a long sloped plane is preferably to reduce circumferential resistance or friction forces. For example, a linear movement of 7 mm is achieved by a rotational movement of approximately 45 degrees (360 divided by 8 jaws), which is quite a steep slope angle that requires more turning force to overcome. Therefore, the effectiveness of this type of device is substantially limited.

In recent years, a variety of prosthetic valves have been developed wherein a valve structure is mounted on a stent and then delivered to a treatment site via a percutaneous catheterization technique. Prosthetic valves are typically much larger in diameter relative to coronary stents. For example, a typical coronary stent diameter is only 1.5 to 4.0 mm in its expanded size, while a stented prosthetic valve diameter will typically be in the range of about 19 to 29 mm, at least 5 times as large as a coronary stent. In another difference, coronary stents are stand-alone devices while, in prosthetic valves, the stent functions as a scaffold to hold the valve structure. The valve structure is typically made of biological materials such as pericardium valves or harvested valves. For improved function after deployment, it is often desirable to preserve such valves in the open (i.e., expanded) diameter inside a preserving solution. Using this procedure, it may be necessary to crimp the valve in the operation room a few minutes before implantation, therefore precluding pre-crimping by the manufacturer over a balloon.

Due to the unique crimping requirements for stent-based prosthetic valves, it has been found that existing crimping devices configured for use with coronary stents are not suitable for use with stent-based prosthetic valves. In addition, as discussed above, existing crimping mechanisms suffer from a variety of shortcomings which limit their ability to be adapted for use with stent-based prosthetic valves. Due to the deficiencies associated with existing crimping technology, a new crimping device was developed by Percutaneous Valve Technologies, Inc. (PVT) that is better suited for use with stent-based prosthetic valves. This crimping device is described in co-owned U.S. Pat. No. 6,730,118 to Spenser, et al. and relates to a crimping device that is adapted to crimp a prosthetic valve as part of the implantation procedure.

Another version of a prosthetic heart valve crimper is marketed by Machine Solutions Inc. of Flagstaff, Ariz. The HV200 is a disposable crimper that uses multiple pivoting segments to crimp percutaneous heart valves. The Machine Solutions crimpers are also disclosed in U.S. Pat. Nos. 6,629,350 and 6,925,847, both to Motsenbocker. These crimping devices are based on segments which rotate about pivot pins to create radial compression. Unfortunately, the pivoting design tends to concentrate stress in certain areas of the individual segments, and in the mechanism for pivoting them. Also, the user must apply significant force to close the crimper aperture around a relatively large percutaneous heart valve.

Although the heart valve crimping technology available to date provides an improvement over the existing stent crimper technology, it has been found that a need still exists for a more effective device. It is desirable that such a device be capable of crimping a valve from a diameter of about 29 mm to a crimped size of about 6 mm without requiring excessive force and without inducing high mechanical stresses within the device. It is also desirable that such a device is simple to use and relatively inexpensive to manufacture. It is also desirable that such a device be sterile and suitable for manual operation in a catheter lab or operating room. The present invention addresses this need.

SUMMARY OF THE INVENTION

The present invention provides a method and apparatus for crimping expandable prosthetic heart valves having support frames and stents.

While the present invention is particularly well-suited for use with stented prosthetic heart valves, such as a prosthetic aortic valve, it can also be applied to other types of large stents such as coronary stents, peripheral stents, other stented heart valves, venous valves, and stent grafts.

A main aspect of the present invention is the introduction of an improved crimping device and method of use, based on jaws with a linear movement toward a center, a stationary base including guidance slits facing the center, and a rotating mechanical member rotating around the center, the member including a spiral track.

In one preferred embodiment, the jaws are activated by the rotating mechanical member. The forces applied to the moveable jaws are predominantly in the radial direction. When crimping a stented valve in a symmetrical way, thus reducing its diameter, (as opposed to crushing and flattening) the radial forces are efficient and effective in evenly reducing the circumference of the prosthetic valve. Accordingly, the force applied to the jaws by the operator via an additional mechanical member is in the same vector and opposite to the stents reaction force while being crimped. This advantageously provides maximum efficiency to the crimping process.

Another preferred aspect is the use of a rotating plate including a spiral track, as the mechanical member, which translates the force of the operator, to the jaws. The gradually spiral-sloped track, in this case 225 degrees, reduces resistance to the crimping operation such that approximately 5 times less force is required by the operator than previous designs.

Another main aspect of the present invention is the guiding slits which, in addition to the activating spiral track described above, assure that the jaws move in a linear manner. In the present invention, each jaw has two guiding slits, a main one in the center of the line of force application/reaction, and the other parallel to the main slit.

Another main aspect of the present invention is the design of the spiral in a way allowing more than one thread to be used to activate the jaws, the benefit of this feature is both in the ability to build a crimper in a reasonable size and in the cost of the production of the crimper.

Another main aspect of the present invention is the capacity to activate the jaws in a symmetrical way from both sides of the jaw, while leaving the middle section of the jaw free.

Another main aspect of the present invention is a novel design that allows activating the jaws by more than one contact point, this allows applying a smaller force to each contact point resulting in the possibility of making the part from relatively inexpensive plastic materials, thus helping to reduce the overall price of the product. Making the device inexpensive allows making the device disposable, which is an important aspect of the invention.

Another main aspect is the arrangement of the jaws from the aspect of their angles. Since the jaws travel inside the said guidance slits and are activated by the spirals, the operators force is translated into the jaw via the contact points. The selected number of jaws with a constant distance relation between the jaws dictates a certain angle of spiral.

Another aspect of the crimping mechanism is a stopping mechanism preventing the operator from over crimping the device by mistake.

In another embodiment, a crimping mechanism includes a rotational member activated by a rotating handle and a pinion gear which allows rotating the member more than 360 degrees. The rotational member is activated by a lever handle and the stationary part is connected to a base. This configuration is advantageous for several reasons. For example, the arrangement allows a larger transmission ratio, and eliminates side forces on the whole apparatus resulting from the manual forces applied by the user, which tend to move the apparatus on the table. If the crimper is activated by two rotating members on both sides of the jaws, both members are connected by a bridge, which will restrict the possible movement of the handle to less than 360 degrees.

One preferred aspect of the invention is a prosthetic valve crimping device capable of reducing the diameter of an expandable prosthetic valve having a support frame by at least 10 mm. For example, prosthetic heart valves expand up to about 29 mm, and may be crimped with the device of the present invention down to about 6 mm, which is a 23 mm reduction. The device comprises a base and housing fixedly mounted thereto, the housing defining a central axis and having at least six evenly spaced spoke-like guide channels, the guide channels each being at least 5 mm in length. A plurality of circumferentially arrayed nesting jaws are axially and rotatably constrained by but radially movable within the housing. Each jaw has a camming member that extends axially into a guide channel, the number of jaws being the same as the number of guide channels, each jaw being substantially radially oriented and being formed of a single piece. Each jaw defines an inner end that has a partial crimping surface which combines with the same on the other jaws to form a crimping aperture of variable diameter and having an axial and dimension sufficient to crimp an expandable prosthetic valve. Each partial crimping surface terminates on one side at a point that is constrained to move along a radial line as the jaw moves along the guide channel. A camming plate rotates about the housing and has a plurality of cams, at least one for each jaw, which act directly on the camming members and move the jaws without any intervening connecting members. A manual actuator rotates the camming plate and simultaneously moves the jaws in to reduce the aperture diameter by at least 10 mm to crimp an expandable prosthetic valve placed within the aperture, and subsequently out to release the valve after crimping.

Desirably, each jaw includes a linear slide that fits within the guide channel, and the guide channels are oriented along radial lines from the central axis. The camming member on each jaw may be located along a radial line from the central axis and extend through a guide channel on the housing, the jaw further including a linear tab parallel to but offset from the radial line that fits within a secondary guide channel on the housing. Each jaw preferably comprises an outer head portion from which the camming member extends and an inner generally circumferentially oriented finger with a recess defined therebetween, and wherein each jaw nests within the recess of an adjacent jaw and the partial crimping surface is defined on a radially innermost face of the finger. In one embodiment, the housing flanks the jaws and defines guide channels on both axial sides thereof, and each jaw includes at least one camming member extending on each axial side to engage a guide channel. Each jaw may have two camming members extending axially from at least one side, wherein the camming plate includes cams that engage each of the two camming members. The cams and the camming plate may be spiral tracks that act to displace each of the camming members radially inward. Preferably, each camming plate includes a plurality of overlapping spiral tracks and each jaw includes two camming members extending axially from at least one side into different spiral tracks. Each of the spiral tracks preferably extends angularly at least 360°.

Another aspect of the invention is a prosthetic valve crimping device capable of reducing the diameter of an expandable prosthetic valve having a support frame. The device includes a housing defining a central axis and having at least six evenly spaced spoke-like guide channels. A plurality of circumferentially arrayed jaws are axially and rotatably constrained by but radially movable within the housing. Each jaw has a camming member that extends into a guide channel, the number of jaws being the same as the number of guide channels. Each jaw is substantially radially oriented and formed of a single piece having an outer end and an inner end. Each jaw inner end has a partial crimping surface which combines with the same on the other jaws to form a crimping aperture of variable diameter and with an axial dimension sufficient to crimp an expandable prosthetic valve. A camming plate rotates about the housing and has a plurality of spiral cams which act directly on the camming members and move the jaws without any intervening connecting members. The spiral cams extend around the axis through an angle of at least 60° to provide a sufficient mechanical advantage to crimp expandable prosthetic valves. A manual actuator rotates the camming plate and simultaneously moves the jaws in to crimp an expandable prosthetic valve placed within the aperture, and subsequently out to release the valve after crimping.

In accordance with a still further advantageous aspect of the invention, a disposable, portable crimping system is provided for prosthetic valves. The system includes a base and a valve crimper mounted on the base having a housing and a plurality of jaws radially movable within the housing. Each jaw defines an inner end that has a partial crimping surface which combines with the same on the other jaws to form a crimping aperture of variable diameter. Each jaw has an axial dimension sufficient to crimp an expandable prosthetic valve. A stop-limited actuator simultaneously moves the jaws in to reduce the aperture diameter by at least 10 mm to crimp an expandable prosthetic valve placed within the aperture, and subsequently out to release the valve after crimping. The system further has a support frame gauge mounted on the base having a tapered throughbore with a minimum diameter that is equal to the minimum aperture diameter as limited by the stop. Finally, a balloon gauge mounted on the base has a throughbore with a diameter sized to calibrate a balloon expanded therewithin to a maximum diameter sufficient to expand a prosthetic valve.

The system further may include a stop member removably attached to the valve crimper, wherein the support frame gauge and the balloon gauge are removably mounted on the base. The removable stop member, support frame gauge, and balloon gauge may be formed in the same color distinct from the valve crimper. Preferably, each jaw has a partial crimping surface defined on an inner end and ending at a point that lies on a radius, the combination of all of the partial crimping surfaces defining the aperture, and wherein each jaw moves linearly along a line with the point remaining on the radius and the partial crimping surface not rotating. Furthermore, each jaw may comprise an outer head portion and an inner generally circumferentially oriented finger with a recess defined therebetween, wherein each jaw nests within the recess of an adjacent jaw and the partial crimping surface is defined on a radially innermost face of the finger.

Another aspect of the present invention involves a method of selecting and utilizing a kit for preparing a prosthetic valve for use. The kit preferably includes a crimping mechanism and accessories such as, for example, a handle lever stop member, a balloon gauge, and/or a crimped-valve gauge. Each of the accessories is preferably removably attachable to the crimping mechanism. The stop member provides a physical stop to limit rotation of the lever handle. The crimped-valve gauge is preferably mounted adjacent to the crimping mechanism. After the prosthetic valve is crimped, the prosthetic valve is placed within the gauge to verify that its outer diameter is desirable. The balloon gauge provides a ring having an inner diameter calibrated to the desired maximum size of the expanded balloon used to deliver the prosthetic valve. The balloon gauge allows the operator to determine the amount of saline required to expand the balloon for proper deployment of the prosthetic valve in the patient.

BRIEF DESCRIPTION OF THE DRAWINGS

FIG. 10a illustrates the interaction between two adjacent jaws.

FIG. 10c is a side view illustrating an alternative jaw tip.

FIGS. 11a and 11b are additional exploded views.

DETAILED DESCRIPTION OF THE PREFERRED EMBODIMENTS

The present invention provides an improved crimper for stents or prosthetic valves. The particularly advantageous features of the present crimper enable reduction in diameter of relatively large stents or prosthetic valves. The crimper is especially suited for crimping prosthetic heart valves which have expanded diameters significantly larger than most stents currently in use. According to Chessa, et al., the Palmaz-Genesis XD stents (Cordis J&J Interventional Systems Co.) are designed for an expansion range of 10-18 mm, and are considered as either large or extra-large stents (see, Results and Mid-long-term Follow-up of Stent Implantation for Native and Recurrent Coarctation of the Aorta, European Heart Journal Volume 26, No. 24, Pp. 2728-2732, published online Sep. 26, 2005). The most frequently used stents are significantly smaller, in the 3-6 mm range. Crimpers for these stents have proved inadequate for reducing in size even larger prosthetic valves, such as the stented prosthetic heart valves. Conversely, aspects of the present crimper may be applicable for use in crimping stents as well, although certain features described herein make it particularly well-suited for crimping large diameter stents, stent grafts, and prosthetic valves.

The term "stented valve" as used herein refers to prosthetic valves for implant, primarily prosthetic heart valves but also conceivably venous valves and the like. A stented valve has a support frame or stent that provides primary structural support in its expanded state. Such support frames are typically tubular when expanded, and may be expanded using a balloon or due to their own inherent elasticity (i.e., self-expanding). An exemplary stented valve is illustrated with respect to FIGS. 14 and 15, although the present invention may be useful for crimping other such prosthetic valves.

Figure 1:
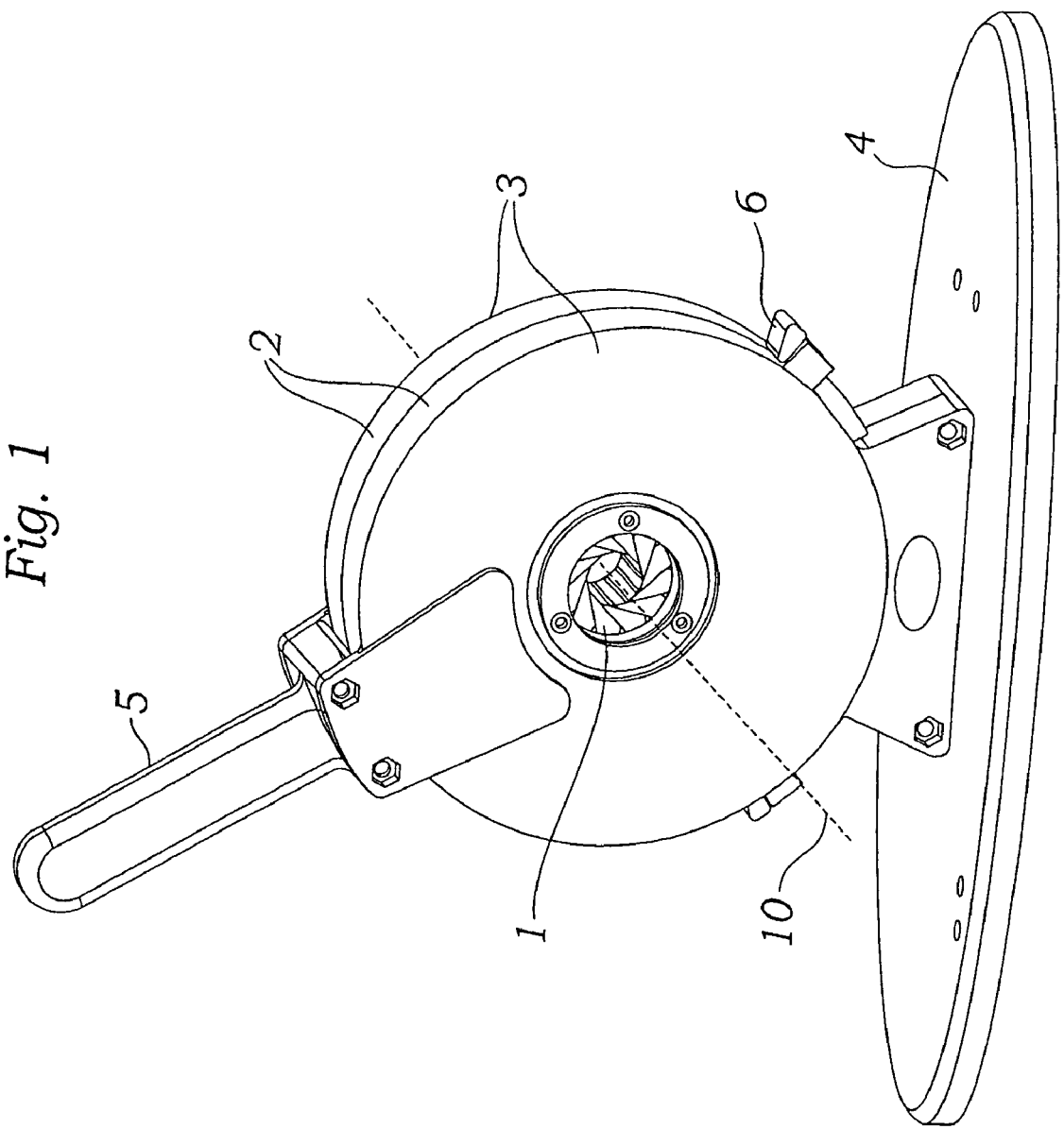
FIG. 1 is a perspective view illustrating one preferred embodiment of an improved crimping mechanism.

With reference now to FIG. 1, one preferred embodiment of an improved prosthetic heart valve crimping mechanism is shown. The crimping mechanism is formed with twelve jaws 1 arranged about the axis 10. The jaws are shown in a semi-closed position defining a variable-sized aperture between their inner ends. The crimping mechanism has a stationary portion comprising a split or two-part housing 2 and a base 4. The stationary portion supports first and second rotational members or plates 3 which are rotated about a central axis 10 by an actuator or lever handle 5.

Figure 2:
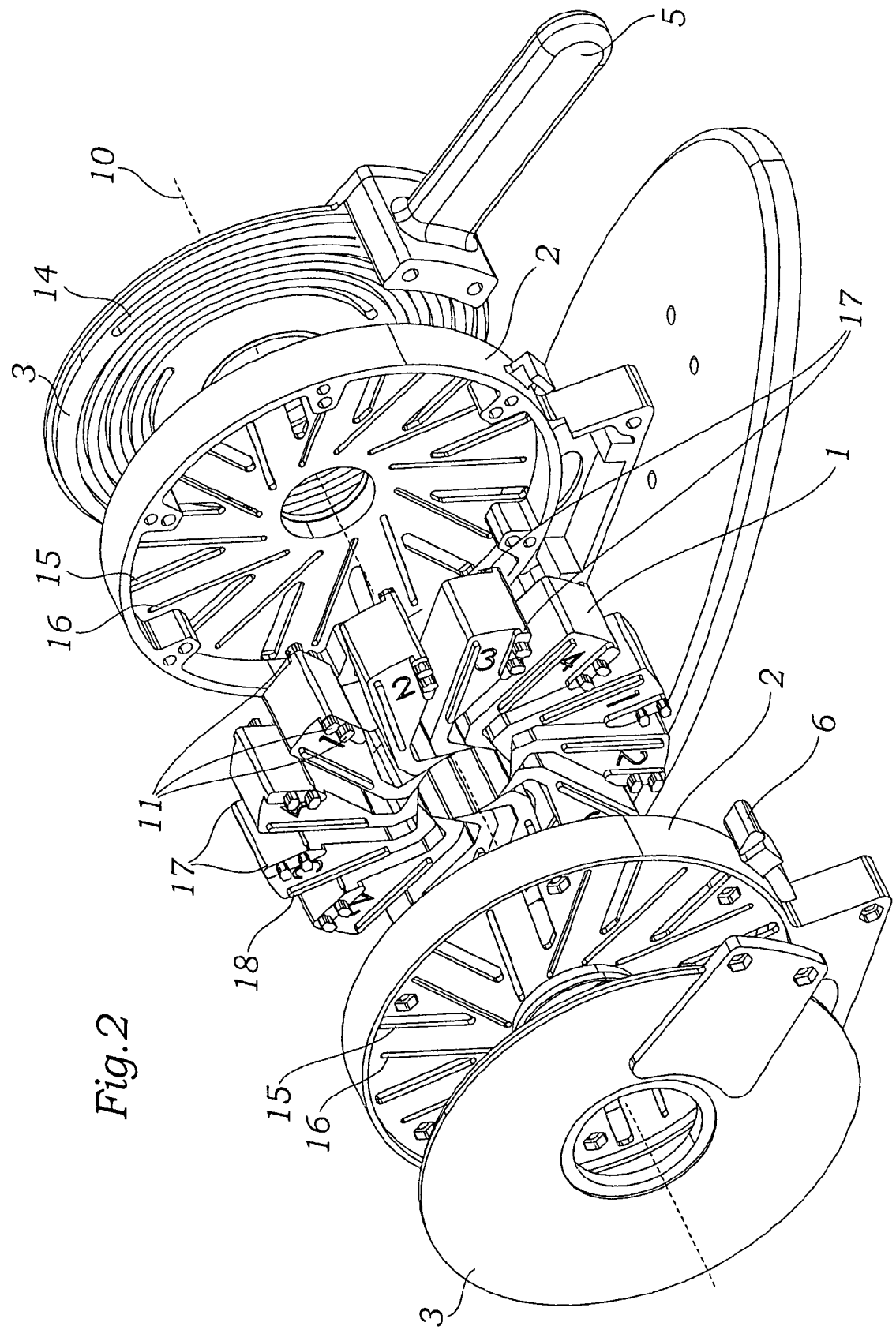
FIG. 2 is an exploded perspective view showing the components of the crimping mechanism.

With reference now to FIG. 2, an exploded view of the crimper mechanism is provided. From this view, it can be seen that the jaws 1 are arranged about the central axis 10 and that the two parts of the housing 2 flank the jaws on both sides. Each part of the housing 2 comprises a generally disk-shape with radially-oriented circular wall and an outer rim extending toward the opposite housing part. The outer rims of both housing parts 2 contact one another and surround the jaws circumferentially. The assembly of the housing parts 2 therefore defines a generally cylindrical cavity therewithin that constraints the jaws 1, however the axial dimension of the jaws 1 is such that they are restrained between the inner faces of the two circular walls of the housing parts 2 with sufficient clearance to enable sliding movement therein. As will be shown and described below, the housing parts numeral to rotationally constrain each of the jaws 1 so as to permit only radial movement.

Figure 9:
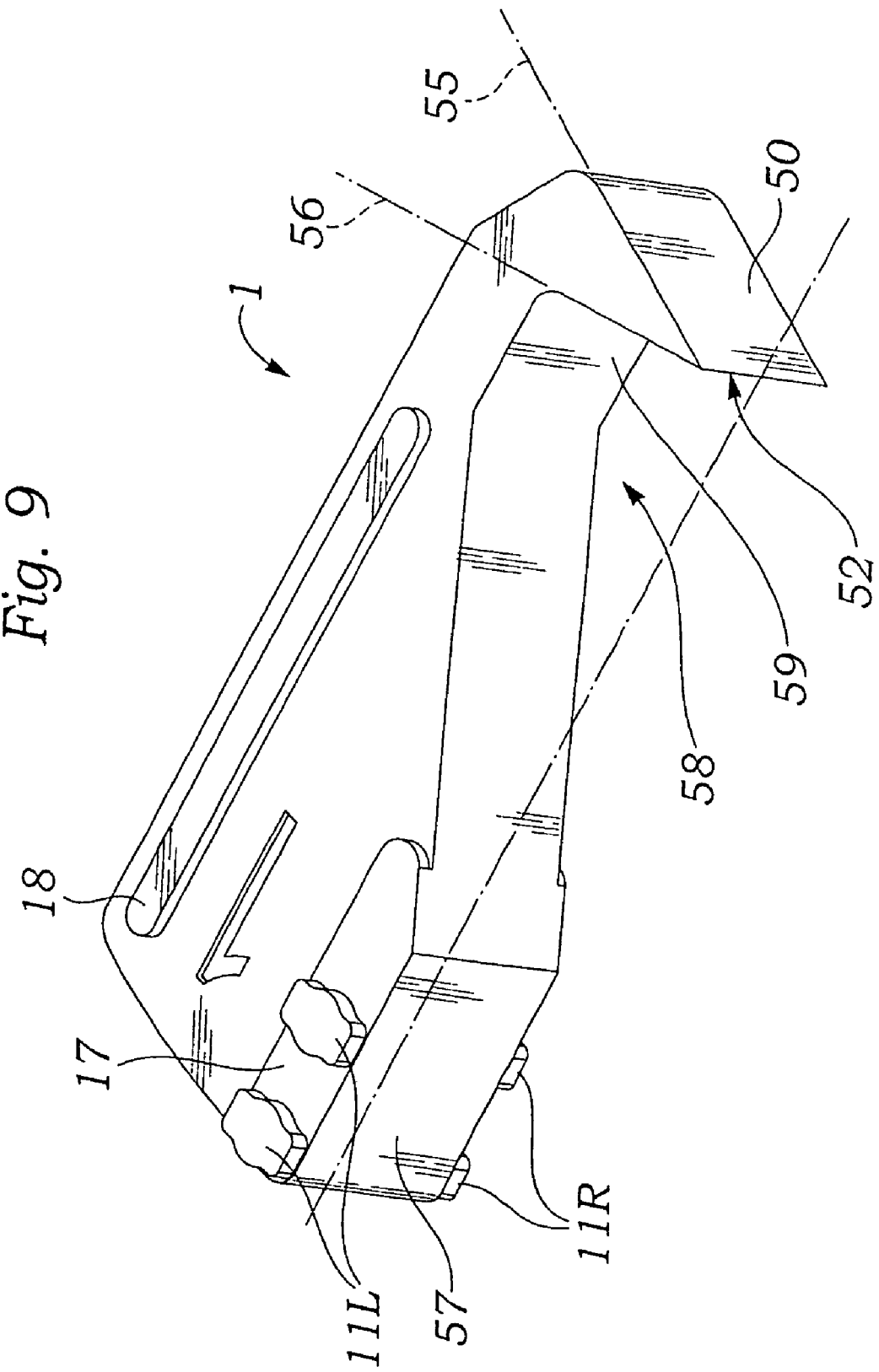
FIG. 9 illustrates a single jaw configured for use with the crimping mechanism.

As seen in FIG. 2 and in detail in FIG. 9, each jaw 1 is preferably provided with a pair of guiding slides 17 outwardly-directed on both axial sides near the radially outermost extent of the jaw. The guiding slides 17 extend through and interact within guiding slits 15 in each stationary housing part 2 to constrain the jaws to linear sliding movement toward and away from the central axis 10. Secondary elongated guiding tabs 18 extend from both sides of each jaw 1 into engagement with parallel secondary slits 16 located in each stationary housing part 2. All four of the guiding slides 17 and guiding tabs 18 in each individual jaw are parallel, as are the corresponding four slits 15, 16. The resulting assembly constraints movement of the jaws 1 within the housing 2 to follow the slits 15, 16, which are generally radially oriented. In fact, the spoke-like slits 15 exist on radial lines outward from the center of the crimping mechanism, while the secondary slits 16 are parallel but slightly spaced therefrom.

Rotation of the first and second outer rotational plates 3 causes translation of the jaws 1 and thus crimps the valve. Both plates 3 are journaled to rotate on the adjacent housing part 2 about the axis 10. The handle 5 attaches through a bracket arrangement to both plates 3 so as to rotate them in tandem. Spiral cuts, grooves or tracks 14 in each rotational plate 3 are provided on each side of the crimper mechanism for translating rotational movement of the lever handle 5 into linear movement of the jaws 1. The spiral tracks 14 are desirably formed between spiral walls extending inward from the rotational plates 3. The spiral tracks 14 interact with activating pin-shaped camming members 11 located on both sides of each jaw, in particular extending outward from each guiding slide 17.

With reference again to FIG. 4, a section of the crimping mechanism is illustrated through the rotational plate 3 such that the cooperation with the activating camming members 11 can be seen. Upon rotation of the outer plates 3 (clockwise in this view) the spiral tracks 14a, 14b, and 14c apply a generally radially inward camming force, shown by the arrows 41, to the activating camming members 11. The lines 42 illustrate the instantaneous tangents to the spiral track 14, which is approximately perpendicular to the direction of motion (i.e., toward the central axis 10) of the jaws and the activating camming members 11.

The geometrical constraints produce the motion of the activating camming members 11, and thus the jaws 1, toward the central axis 10. Furthermore, the jaw motion is constrained by the cooperation of the guiding slits 15, 16 and slides 17 and tabs 18 and by the jaw geometry itself, which will be further discussed with reference to FIGS. 9 and 10.

Figure 3:
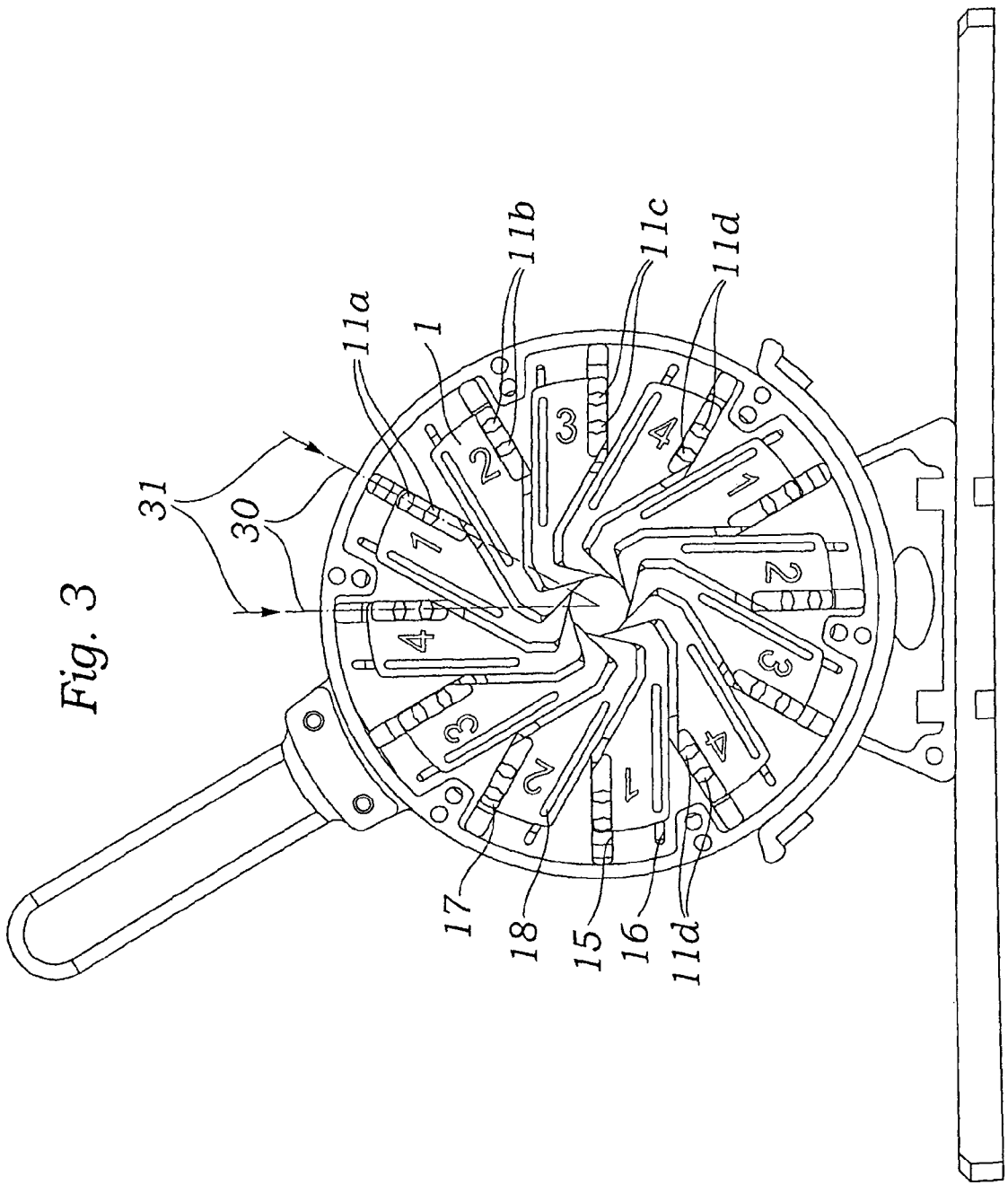
FIG. 3 is a side view illustrating the cooperation of the components.
Figure 4:
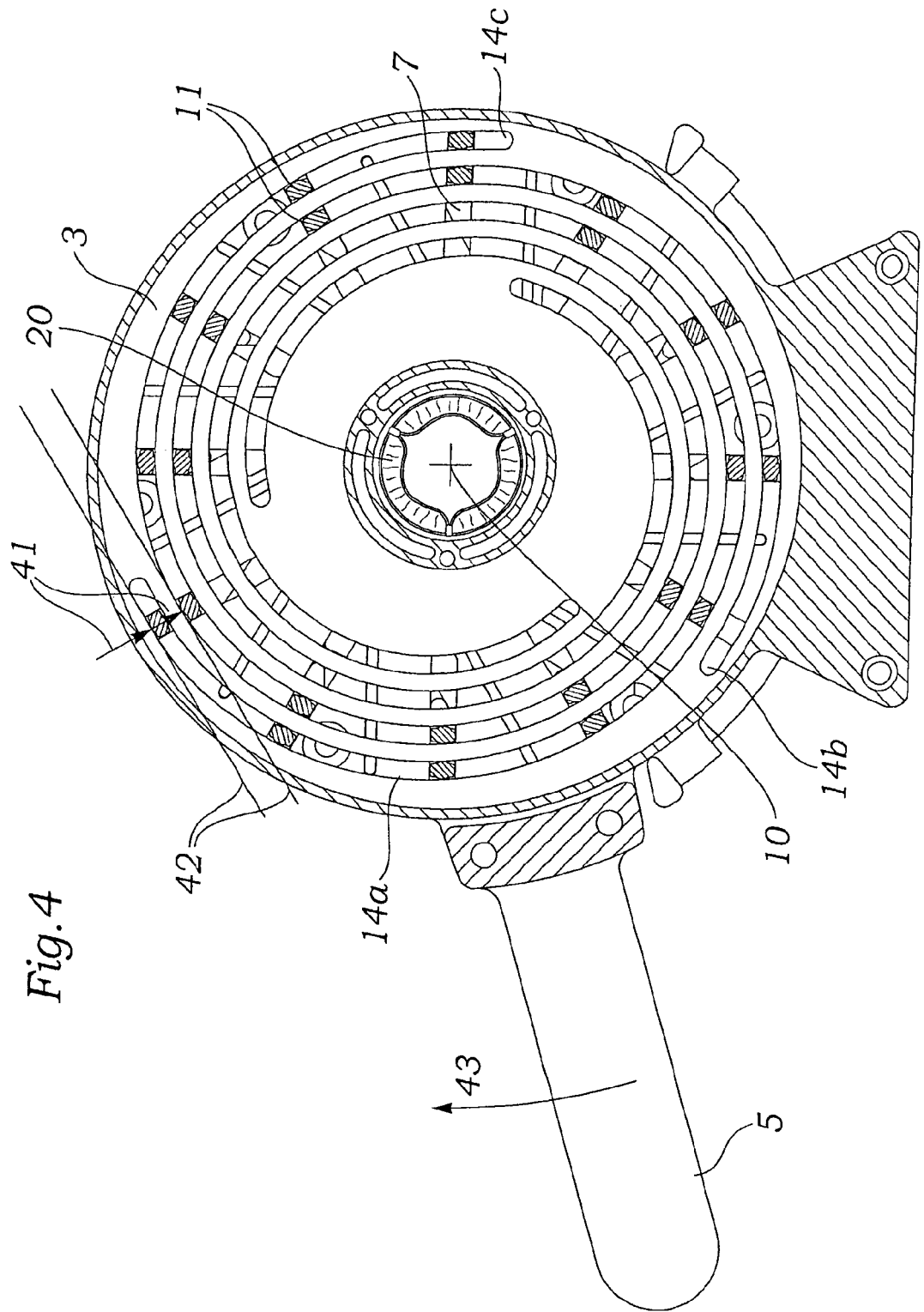
FIG. 4 is a side view illustrating the spiral track configured for moving the jaws.
Figure 5:
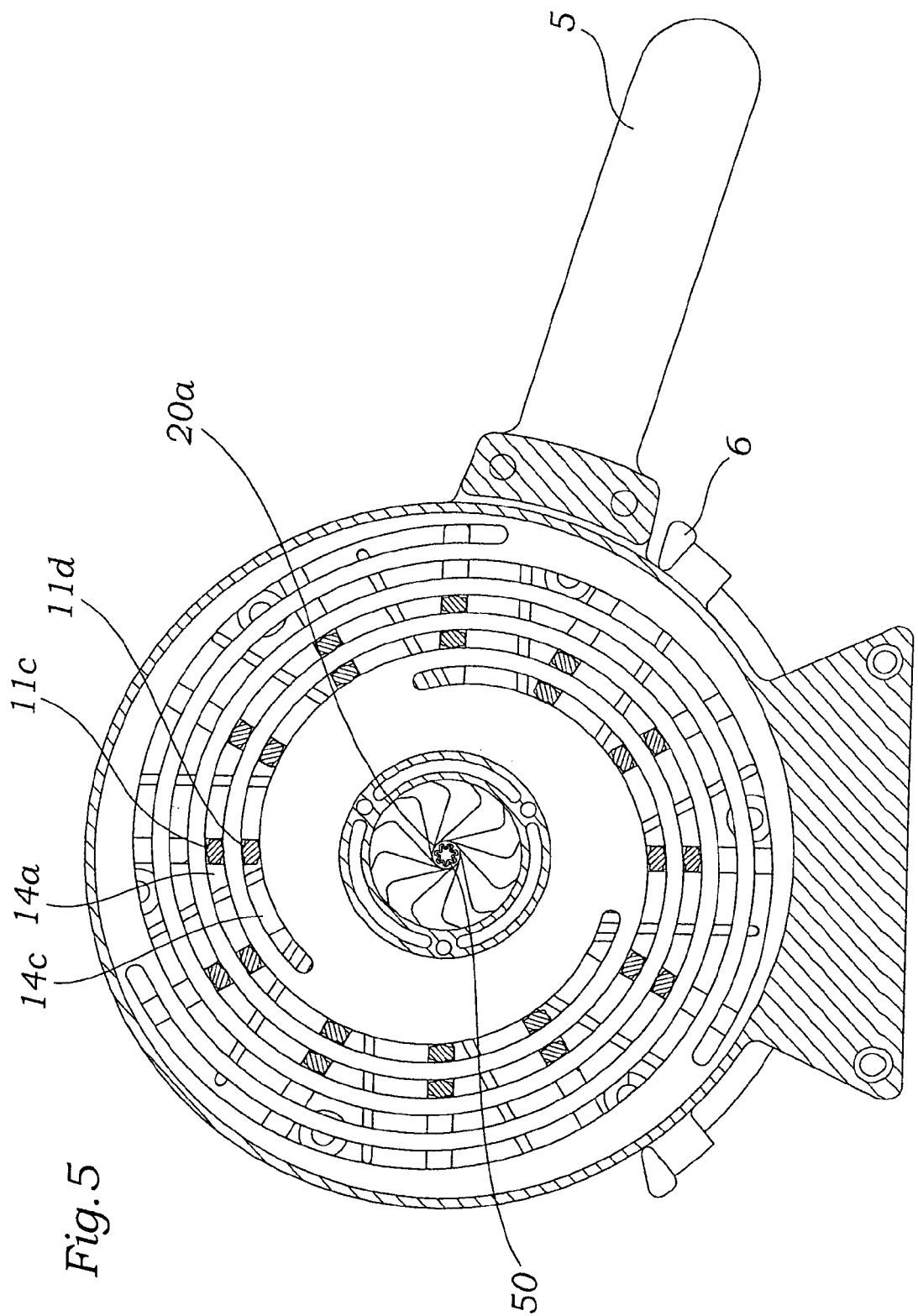
FIG. 5 is a side view illustrating the jaws in the closed position.
Figure 7:
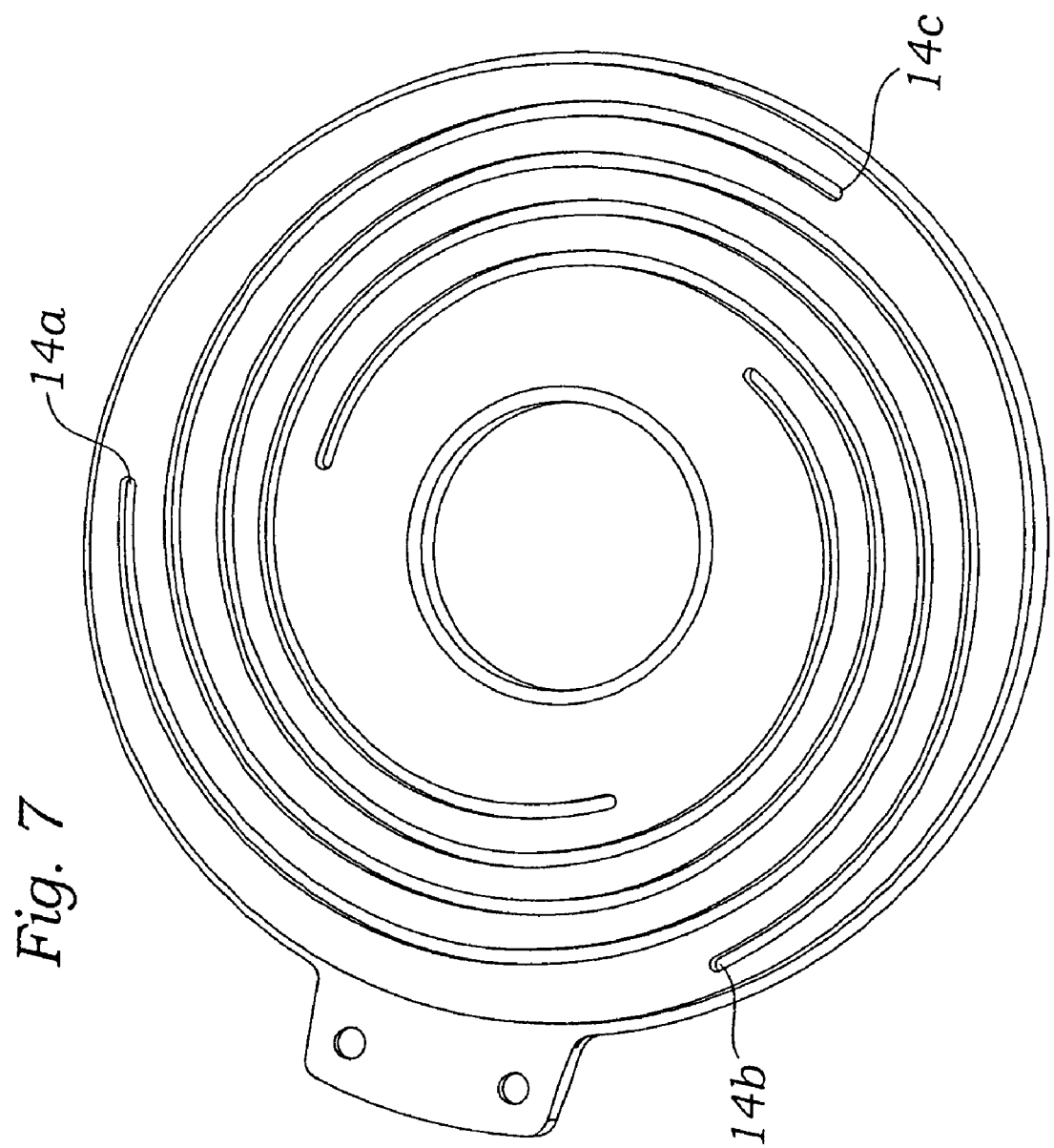
FIG. 7 illustrates a first cover formed with a spiral track.

When the lever handle 5 is rotated in the direction of the arrow 43 in FIG. 4, the rotational plates 3 rotate, thereby causing the spiral tracks 14 to rotate. This rotational movement of the spiral tracks pushes the jaws inward, thereby closing the aperture 50 (FIG. 5). Movement of the jaws 1 toward the center produces crimping the stented valve 20. FIG. 4 and FIG. 7 showing one of the rotational plates 3 in isolation best illustrate the shape and distributions of the three independent spiral tracks 14a, b and c, which fit geometrically the three sets of four jaws described in FIG. 3.

With reference now to FIGS. 3 and 4, a cross-sectional view of the crimping mechanism is provided wherein the jaws 1 are shown in a partially open position. As discussed above, the twelve jaws 1 are arranged in a circular configuration around the central axis 10. The lines of movement of the jaws are shown for two jaws by the dashed lines 30, and their respective crimping movement directions by the arrows 31. The linear guiding slides 17 and tabs 18 are also seen here positioned within respect to the guiding slits 15 and 16. Three sets of jaws numbered from 1 to 4 are illustrated. The difference between the jaw positions relates to the placement of the camming members (see 11a-11d), two of which on the each side of each jaw 1 are held within the spiral tracks 14 on the rotational plates (see element 3 in FIG. 2). In the exemplary embodiment, therefore, there are four camming members 11 acted on by four spiral tracks 14 for each jaw 1.

In this example, there are three separate spiral tracks 14a, 14b, 14c formed in each rotational plate 3. Each spiral track 14 extends from a point near the outer periphery of the plate 3 and terminates inward therefrom at a radial location identical to the termination points of the other tracks. The pitch of the tracks is constant and the three tracks are cut symmetrically, therefore a constant distance between the camming members creates a geometric match with the tracks, although each camming member is being activated by a different track. The respective starting and ending points of the tracks 14 are evenly circumferentially spaced, in this case 120° apart. Each spiral track 14 extends more than 360°, preferably around 450°, around the axis 10. This relatively shallow spiral helps reduce the amount of force required to rotate the lever handle 5 because the tracks contact and apply primarily radial forces to the camming members. Stated another way, increasing the angle of the spiral tracks 14 makes the mechanism harder to operate since the angled spirals apply a larger circular or frictional component of force to the camming member contact points.

FIG. 5 is a view similar to FIG. 4 but with the lever handle 5 fully rotated toward a stop member 6 which prevents further rotation. The jaws aperture 50 is closed to the extent needed to fully crimp the stented valve 20a. The dual activating camming members 11, for each jaw 1 are seen fitting in different spiral tracks 14, but farther radially inward within the spirals. For example, camming member 11c fits into track 14a and camming member 11d fits into track 14c.

There are a total of twelve jaws grouped in three identical sets of four jaws, as labeled in FIG. 3. FIG. 4 illustrates in cross-section section the evenly circumferentially spaced sets of two camming members 11 on one side of each jaw 1. The two camming members 11 on each side of each jaw 1 project into different spiral tracks 14. Additionally, because of the nature of the spiral tracks 14 and space limitations the camming members 11 of adjacent jaws are slightly radially offset from one another. For example in FIG. 4, spiral track 14c terminates close to the 3:00 position with a middle portion of spiral track 14b immediately radially inward therefrom. One of the two camming members 11 in a jaw 1 oriented at precisely the 3:00 position engages outer track 14c while the other engages adjacent track 14*b*. Looking counterclockwise, the two camming members 11 in a jaw 1 oriented at the 2:00 position also engage these two tracks 14*b*, 14*c*, which have now spiraled inward a short distance. Continuing further counterclockwise, jaws 1 at the 1:00 and 12:00 positions have camming members 11 that are still further radially inward along the same two spiral tracks 14*b*, 14*c*. At 11:00, one of the camming members 11 engages spiral track 14*a* while the other engages spiral track 14*c*. This pattern continues around for each set of four jaws 1.

The provision of two separate camming members 11 on each jaw 1 reduces the force applied to each camming member, ideally dividing the force in half. Manufacturing tolerances may cause one of the spiral tracks to contact one of the camming members earlier than the other pair, but ultimately both camming members are acted upon. Moreover, each jaw 1 desirably has a pair of camming members 11 extending from both sides which are acted upon by spiral tracks 14 in two of the rotating plates 3. Because the camming forces are applied on both sides of each of the jaws 1, there is symmetry to the stresses and less chance of binding and wear from misalignment.

Working prototypes with 6 jaws have been made, though 6 is considered the minimum. The number of jaws desirably ranges between 8-12. The less jaws, the larger each one would have to be to provide the necessary contributory crimping surface in the aperture. Moreover, decreasing the number of jaws affects the circularity of the aperture (more jaws results in a more perfect circle). On the other hand, including more jaws reduces the size of each jaw and increases the complexity of the devices. Ultimately, material strength considerations and cost limit the number of jaws.

Figure 6:
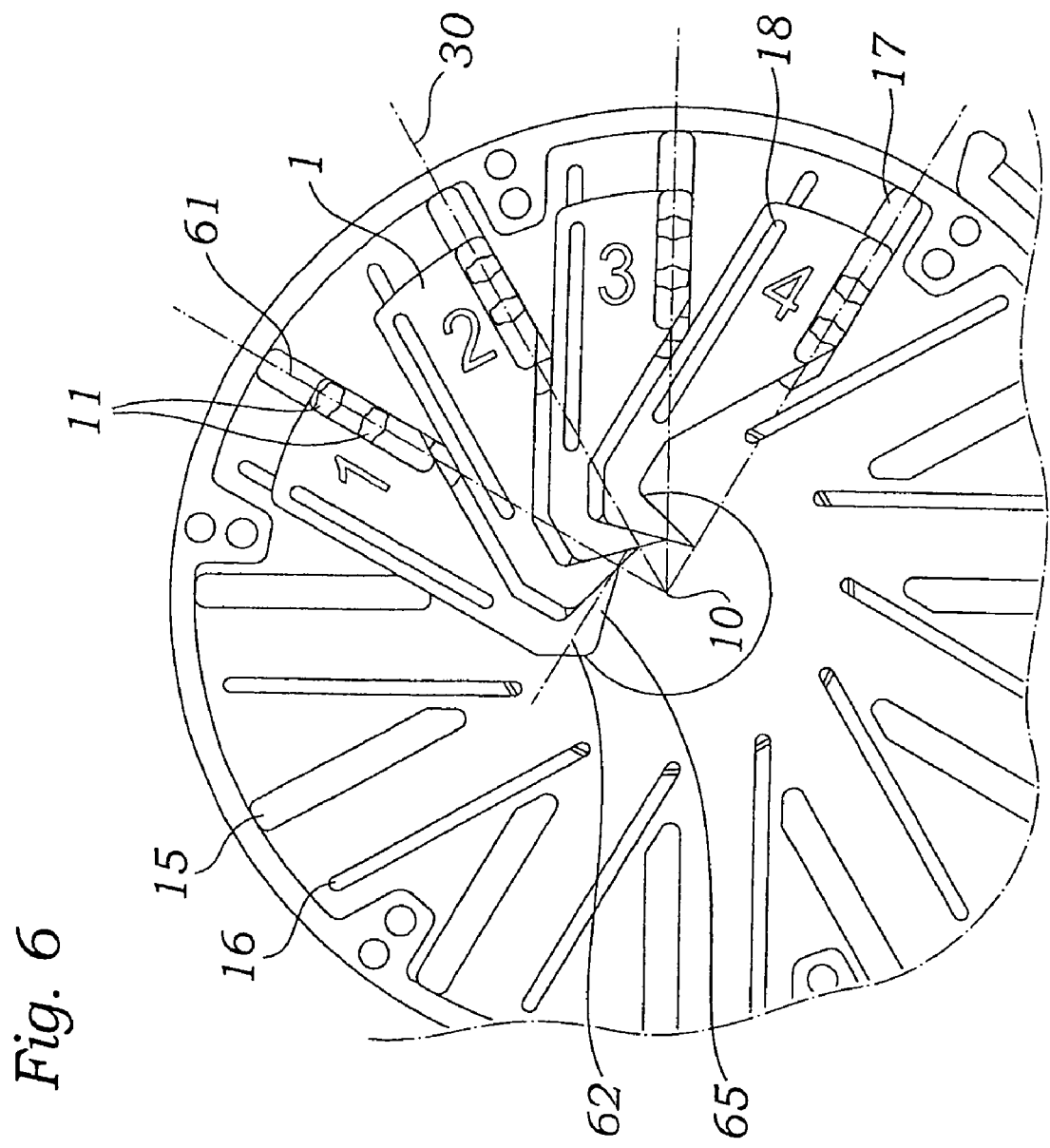
FIG. 6 is an enlarged view illustrating a portion of the jaws.

With reference to FIG. 6, an enlarged view of the jaws 1 is provided wherein the direction of motion 30 of the jaw identified as jaw No. 2 toward the central axis 10 can be seen. The guiding slides 17 and tabs 18 and the guiding slits 15, 16 are seen clearly again. Line 62 illustrates a geometrical symmetry line of the jaw aperture 65, which preferably remains constantly perpendicular to the motion line 61 of the jaw identified as jaw No. 1, which extends through the center of the activating camming members 11.

Figure 8:
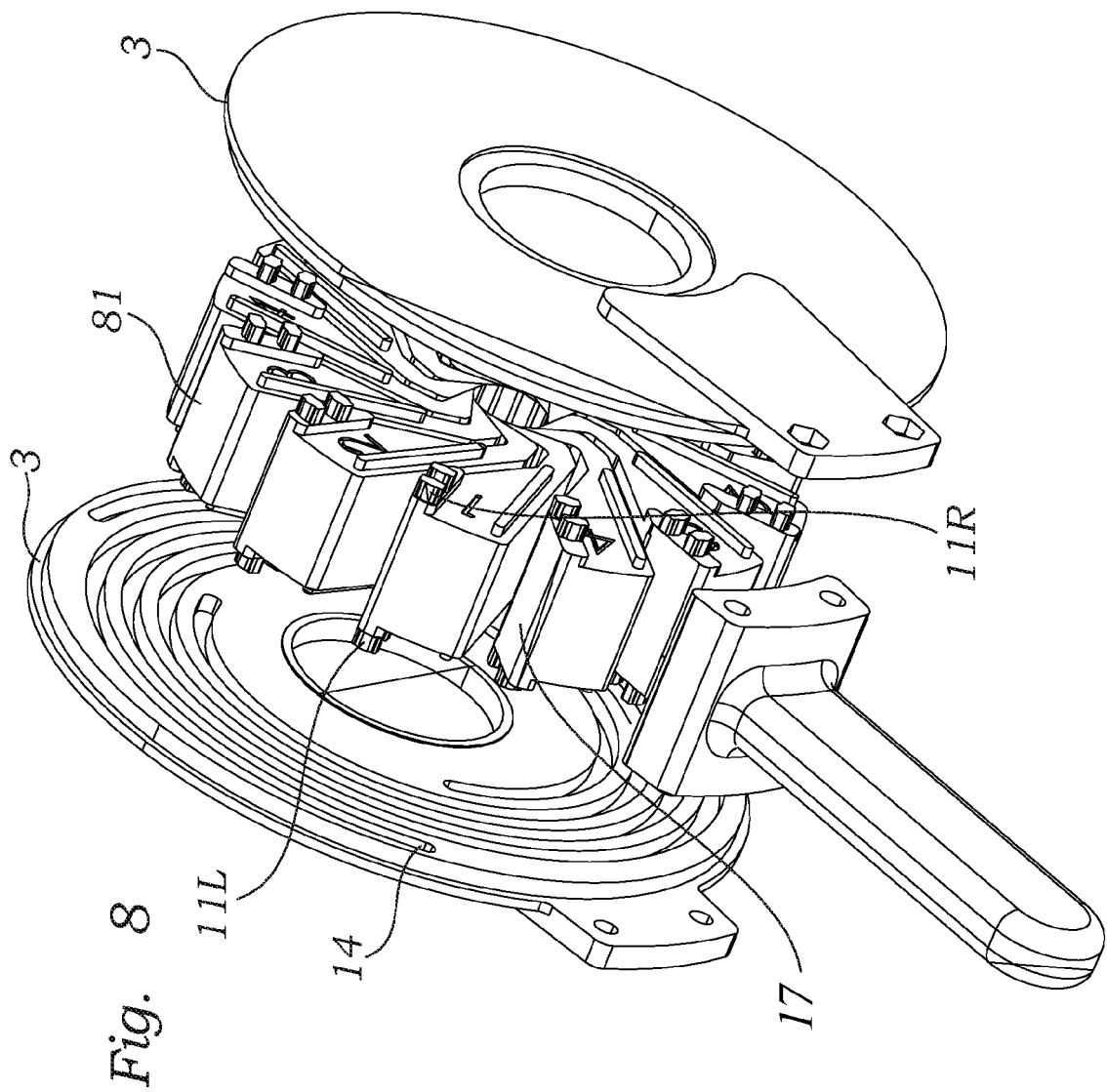
FIG. 8 is another exploded view illustrating the primary components of the crimping mechanism.

With reference to FIG. 8, another exploded view of the crimping mechanism shows the two rotational plates 3 on both sides of the jaws 1 with the housing parts 2 removed. The spiral tracks 14 receive the camming members 11R and 11L located on opposite sides of the jaw identified as jaw No. 1, while allowing an axially central part of the jaw 81 to remain free. This arrangement reduces the stress on each one of the four pins located on each jaw. The device arranged in this way works symmetrically and the danger of self locking, which might occur when activating a jaw from one side only is substantially reduced. Stated another way, the dual-sided jaw actuation creates a balanced net radial force on the jaw without moment (torque) which might otherwise lead to binding.

With reference to FIG. 9, it can be seen that one of the jaws 1 comprises the guiding slides 17 and tabs 18 (on both sides) and the four camming members 11L and 11R. The radially inner end of each jaw defines a wedge-shaped finger 52 defined by axially-oriented faces lying in planes within which lie lines 55 and 56. A portion of the radially inner face of each jaw 1 forms a part of the aperture 50 and is 1/12 of the whole aperture in this example. Each jaw 1 includes a relatively enlarged head portion 57. A cutout or recess 58 narrows the material between the head portion 57 and the finger 52 to a bridge 59.

With reference to FIGS. 6 and 10*a*, to the nesting relationship between the series of circumferentially spaced jaws 1 is shown. This geometric nesting of the jaws provides specific benefits including excellent mechanical leverage between the lever handle 5 and the crimping force applied to the stented valve, reduced complexity of the device, and reduced stresses on each jaw. First a more complete understanding of the jaw geometry is necessary.

Figure 10B:
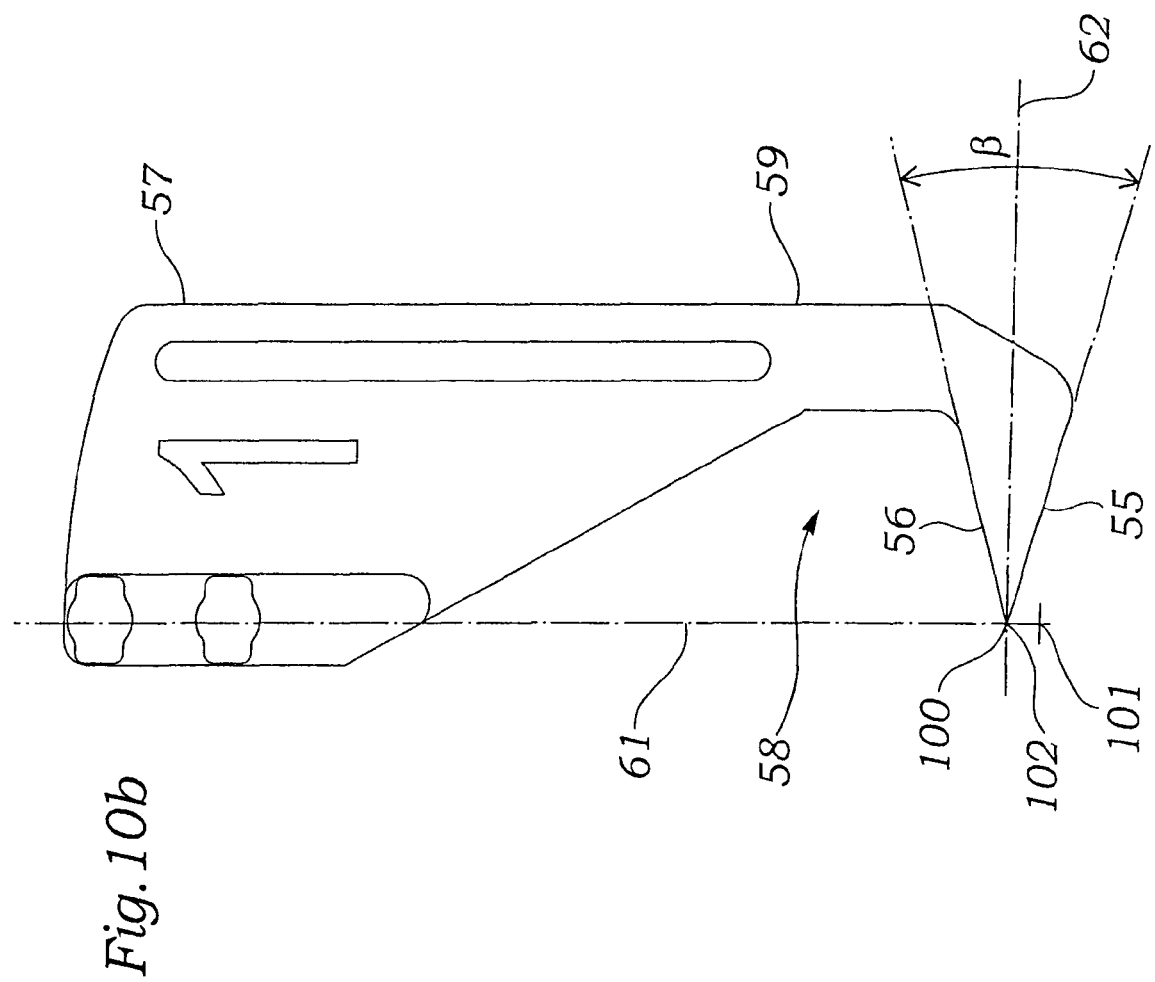
FIG. 10b is a side view illustrating the profile of a preferred jaw.

With reference to FIGS. 10*a* and 10*b*, the geometric relation between the jaws is illustrated. Line 61 illustrates the motion line of the illustrated jaw, having a certain angle α between it and the other jaws. Because there are 12 jaws and the device is symmetrical, the angle α will be 30 degrees. For each jaw 1, the geometrical symmetry line 62 is perpendicular to movement line 61 and bisects the angle formed by adjacent jaw tip lines 55 drawn along the radially inner faces thereof. The radially inner jaw faces extending along the tip lines 55 in turn form the perimeter of the aperture 50 for closing the stent when crimped. Line 56 on the radially outer face of each wedge-shaped finger 52 is a mirror image line of line 55 (about line 62). The geometric restraint is that the outer face of each finger 52 extending along line 55 slides on the inner face of the finger 52 of the adjacent jaw extending along line 56 when closing or opening the jaws in the direction of movement lines 61.

Point 100 is the intersection of lines 61, 62, 55 and 56 and is a geometric position fixed to a jaw, and moves with it when the jaw moves. Point 101 is the intersection of the motion direction lines 61 for all twelve jaws 1. Point 101 corresponds to the axial center 10 of the crimping mechanism and is always constant with respect to all moving and stationary parts of the crimping mechanism. As shown in FIG. 10*c*, it is also possible to add a radius 102 to the jaw tip, which will be selected according to the minimal crimped size.

FIG. 10*b* shows a top view of one jaw. The included angle β between lines 55 and 56 is always identical to angle α shown in FIG. 10*a* and determined by the number of jaws in the crimping mechanism, for example twelve jaws will result in 30 degrees, while six jaws will give 60 degrees.

With reference again to FIG. 3, the lines of force 30, 31 applied to the jaws derived from contact between the spiral tracks 14 and the camming members 11. The lines of force extend directly radially inward, and are such the camming members 11 for each jaw lie on a radial line from the center. FIG. 10*b* shows that the radial line extends through the intersection point 100 which is the apex of the wedge-shaped finger 52. FIG. 10*a* illustrates the radially inner end of jaw "2" nesting into the recess 58 in jaw "1" such that the fingers 52 overlap at the aperture. Indeed, the total surface area of the outer face of the finger 52 of jaw "2" that contributes to the aperture is included within the angle α. Again, because there are 12 jaws the angle α will be 30 degrees (360°/12). Because the outer faces of the fingers 52 are straight, the aperture actually describes a dodecagon. It will thus be seen that reducing the number of jaws incrementally reduces the number of straight sides of the polygon that the aperture 50 describes.

This nested jaw arrangement facilitates the application of a direct radially inward force on each jaw and on each surface of the jaw contributing to the aperture. Importantly, the outer head portions 57 of the jaws 1 are separated and can thus be acted on along different radial lines, but the inner ends nest together with the ramp or wedge-shaped fingers having mating surfaces that permit relative sliding while maintaining contact therebetween. Furthermore, though the wedge-shaped fingers 52 are cantilevered because of the cutout portion 58 of the jaw, the stresses therewithin are made more uniform by the gradually widening cross-section toward the connecting bridge 59. The radially inward forces applied to the camming members 11 travels through the head portion 57, bridge 59, and along the fingers 52. It should be noted that the circumferential width of each jaw 1 is substantially the same from its outer end to its inner end. This unique arrangement permits nesting of the inner ends of the jaws and enables the direct radial application of crimping force to the prosthetic valve.

FIGS. 11a and 11b illustrate an alternative embodiment of the rotational plate 3. Instead of using a lever handle 5 (as discussed above with reference to FIG. 1), the actuator comprises a rotating handle 95 connected to a shaft 96 and pinion gear 97 for rotating a single rotational plate 3. The pinion gear 97 meshes with the gear 98 on the rotational plate. Activating camming members 11 on only one side of the jaw couple to the single spiral track 14 and are guided by the coupling of the guiding slits 15 and 16 to the guiding slides 17 and tabs 18. In this example there are only six jaws 1. Since there is a mechanical advantage provided by the gearing arrangement reducing the necessary activation force, activating jaws on only one side is possible. Furthermore, there is no need for more than one spiral track since there are only six jaws.

Figure 13:
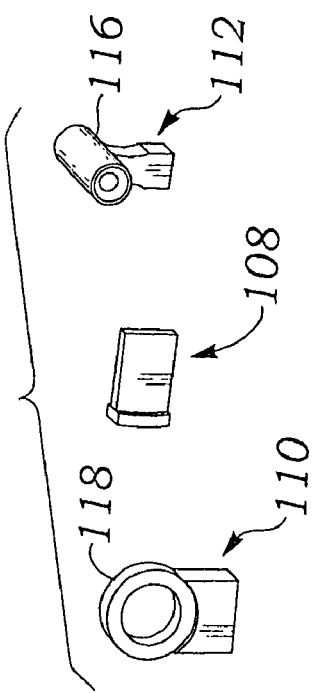
FIG. 13 is an exploded view of the accessories of FIG. 12.
Figure 12:
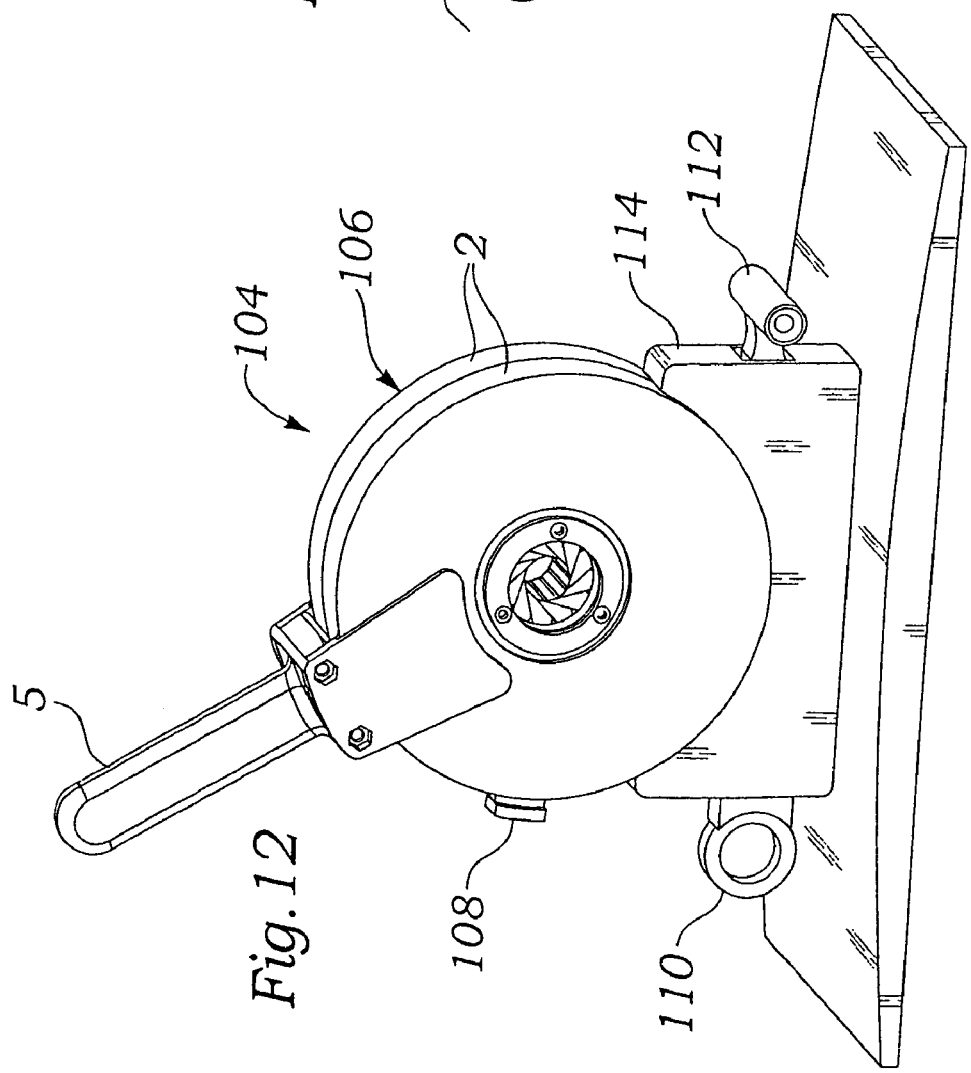
FIG. 12 is a perspective view illustrating one preferred embodiment of a crimping mechanism of the present invention in conjunction with a set of removable accessories unique to a particular valve size.

FIGS. 12 and 13 illustrate an advantageous aspect of the present invention which will greatly reduced manufacturing costs. FIG. 12 illustrates a prosthetic valve crimper system 104 which includes the crimping mechanism 106 described above and three removable accessories seen exploded in FIG. 13. Specifically, the removable accessories include a handle lever stop member 108, a balloon gauge 110, and a crimped-valve gauge 112. Each of these accessories 108, 110, 112 removably attach to the aforementioned crimping mechanism, with the stop member 108 fitting closely within an aperture formed in the housing 2 and the gauges 110, 112 desirably mounting somewhere on a base 114 of the crimping mechanism.

The stop member 108 was previously shown at 6 in FIG. 1 and provides a physical stop to rotation of the lever handle 5 in the direction of a reduced crimper aperture. That is, when the crimping mechanism 106 is operated with an expanded prosthetic valve therewithin, the lever handle 5 rotates in one direction until its movement is prevented by the stop member 108. The size of the stop member 108 is calibrated to stop movement of the lever handle 5 when the proper aperture size is reached for a particular crimping operation. That is, prosthetic valves having various expanded diameters are crimped by different amounts, necessitating different magnitudes of rotation of the lever handle 5. By forming the stop member 108 as separable from the crimping mechanism 106, the same crimping mechanism can be used for different sized valves by just selecting the proper stop member 108 from a set of differently-sized stop members.

A crimped-valve gauge 112 provides a convenient check on the success of the crimping operation. The gauge 112 mounts directly next to the crimping mechanism 106 and, after a prosthetic valve has been constricted thereby, is placed within the gauge 112 to verify that its outer diameter is as expected. If for some reason the crimping mechanism 106 malfunctions or the prosthetic valve springs outward after having been compressed inward, the valve may be too large to be passed through the available delivery catheter or cannula. The crimped-valve gauge 112 provides a tube 116 having a tapered throughbore with a minimum diameter that is equal to the minimum aperture diameter as limited by the stop member 108. The crimped prosthetic valve will typically be mounted over a balloon catheter which is used to pass the prosthetic valve through the gauge 112 after having been crimped. Any inadequacy in the crimping process is then corrected by compression of the prosthetic valves as it passes through the tapered throughbore of the tube 116.

Finally, the balloon gauge 110 provides a ring 118 having an inner diameter calibrated to the desired maximum size of the expanded balloon used to deliver the prosthetic valve (if the prosthetic valve is balloon-expandable). Prior to crimping the prosthetic valve around the balloon, the operator expands the balloon within the ring 118. Expansion of such balloons is typically accomplished by injecting a saline solution into the balloon catheter to fill the balloon. After filling the balloon such that it expands to its limit within the ring 118, the precise amount of saline solution needed for the expansion is known. By withdrawing the saline solution from the balloon and maintaining it in the same syringe that will be used to deliver the prosthetic valve, the clinician insures that the balloon will re-expand to its desired limit.

The prosthetic valve crimper system 104 described above is extremely convenient and flexible. For the clinician, the system provides in one portable device all of the tools necessary to calibrate the delivery balloon, crimp the prosthetic valve around the balloon, and insure that the crimped diameter is accurate. Desirably, the system is primarily constructed of molded plastic parts which are lightweight and also relatively inexpensive to manufacture. Therefore, the cost of the device, which is disposed of after each use, is reduced. For the manufacturer, only one crimping mechanism 104 need be produced along with sets of differently-sized accessories 108, 110, 112.

To make the system even more user-friendly, each set of three accessories 108, 110, 112 is desirably colored differently than other sets. Therefore, the three accessories for a 25 mm (expanded diameter) prosthetic valve may be green, while the three accessories for a 29 mm prosthetic valve may be red. Not only does this facilitate the assembly of the system, but also provides a level of confidence for the clinician that the proper accessories have been supplied.

Figure 14:
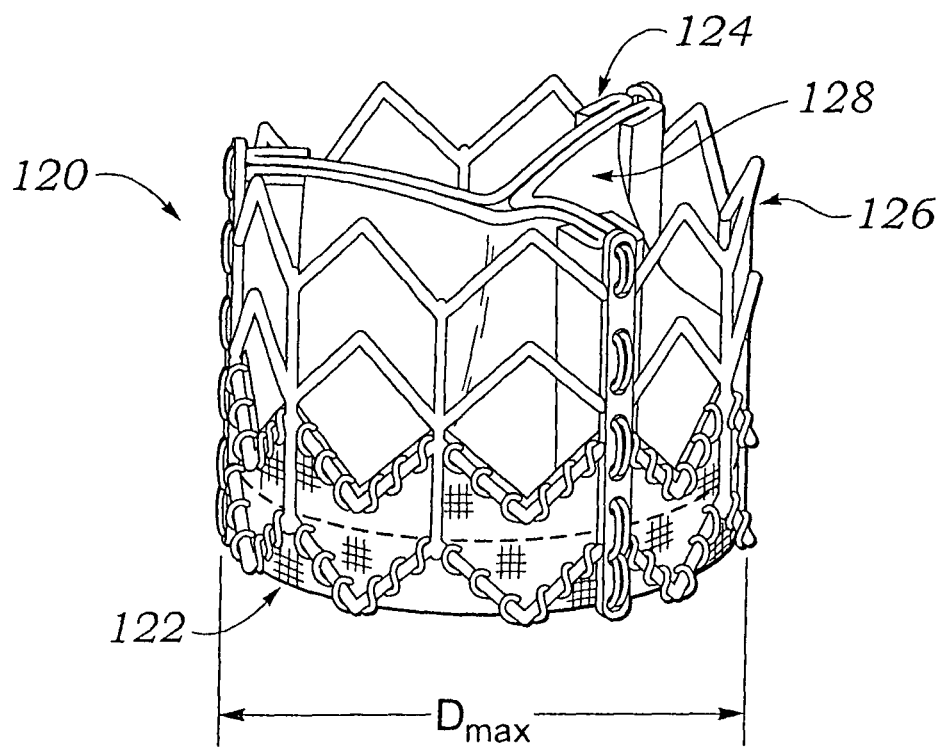
FIG. 14 is a perspective view of an exemplary prosthetic heart valve having an expandable support frame and a plurality of flexible leaflets therewithin.

FIG. 14 illustrates an exemplary balloon-expandable prosthetic heart valve 120 having an inflow end 122 and an outflow end 124. The valve includes an outer stent or support frame 126 supporting a plurality of flexible leaflets 128 within. FIG. 14 shows the valve 120 in its expanded or operational shape, wherein the support frame 126 generally defines a tube having a diameter $D_{max}$, and there are three leaflets 128 attached thereto and extending into the cylindrical space defined within to coapt against one another. In the exemplary valve 120, three separate leaflets 128 are each secured to the support frame 126 and to the other two leaflets along their lines of juxtaposition, or commissures. Of course, a whole bioprosthetic valve such as a porcine valve could also be used. In this sense, "leaflets" means separate leaflets or the leaflets within a whole xenograft valve.

Further details on the exemplary prosthetic heart valves of a similar type can be found in U.S. Pat. No. 6,730,118, which is expressly incorporated by reference herein. In addition, the Cribier-Edwards™ Aortic Percutaneous Heart Valve available from Edwards Lifesciences of Irvine, Calif. is another balloon-expandable prosthetic heart valve of a similar nature, whose construction is also expressly incorporated by reference herein.

Figure 15:
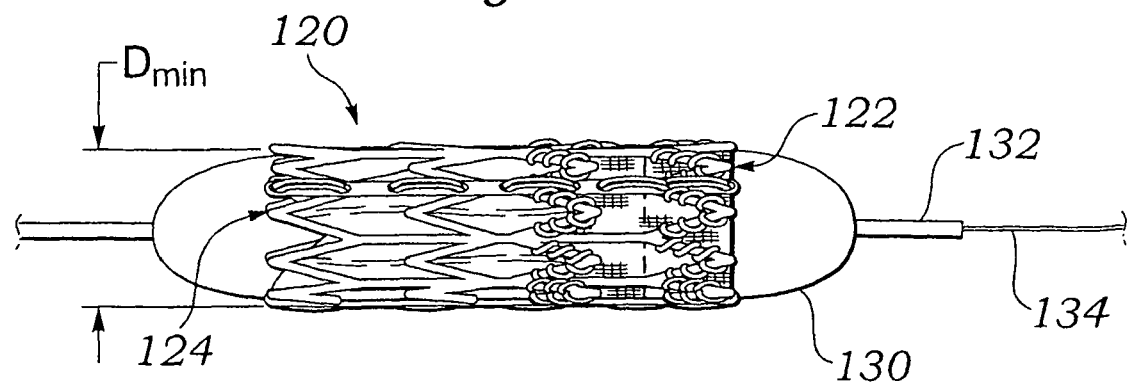
FIG. 15 is a side view of the prosthetic heart valve of FIG. 14 crimped to a reduced diameter around a balloon catheter.

FIG. 15 shows the valve 120 mounted on a balloon 130 prior to inflation. The crimped outer diameter of the valve 120 is indicated at $D_{min}$. The balloon 130 typically mounts on the end of a catheter 132 which is guided to the implant sites over a steerable wire 134.

The crimper mechanism 106 of the present invention efficiently reduces the size of prosthetic valves from up to 30 mm ($D_{max}$) down to 6 mm ($D_{min}$). Prosthetic heart valve sizes are typically anywhere between 20 mm up to about 30 mm. The minimum reduction in size is thus around 14 mm and the maximum around 24 mm. In contrast, typical coronary stents have an expanded diameter of between about 3-6 mm and are crimped down to a minimum diameter of between about 1.5-2 mm, for a total maximum size reduction of around 4 mm. To distinguish conventional stent crimpers, the present invention provides a diameter reduction of at least 10 mm. In the exemplary embodiment, the radial travel of the jaws is limited by the linear spacing between the slides 17 and tabs 18 and associated slots 15, 16. Because diametrically opposed jaws act toward each other to reduce the size of the prosthetic valves, each crimp the valve half the distance of the entire reduction in diameter. Therefore, the minimum length of the slots 15, 16 is 5 mm, though the practical constraint is the freedom of travel of the slides and tabs 17 and 18 within the slots 15, 16, which is at least 5 mm.

The mechanical advantage of the crimper mechanism 106 can be best illustrated by the amount of handle rotation required to crimp a prosthetic heart valve. Specifically, the exemplary embodiment shows handle rotation of approximately 270° causing a maximum prosthetic valve reduction of about 24 mm. At the same time, each of the 12 jaws used to crimp the prosthetic valve translates linearly without intervening linkage between the prime mover rotating plates 3 and the jaws. Lightweight, inexpensive components contribute to ease-of-use and disposability.

In one advantageous feature, the crimping device may be formed of a plastic material to reduce cost and weight. In addition, due to the efficiency of the construction, the crimping mechanism may be manufactured at a relatively low cost. Accordingly, the crimping mechanism described herein is well-suited for single use purposes, thus obviating the need for sterilization between uses.

It should be noted that the particular mechanism for crimping prosthetic valves disclosed herein can be structurally modified in various ways while still performing its essential function. For example, in the exemplary embodiment the jaws move radially but are constrained laterally or rotationally. Camming members on the jaws move along radial channels in a fixed plate, while a rotating plate with a spiral camming track provides the moving force. In a reverse configuration, the jaws could rotate while the spiral camming tracks remain stationary. The radial channels would also have to rotate with the jaws and camming members. The exemplary embodiment is preferred, however, because of the added complexity to the design with rotating jaws. The alternative is mentioned here only to illustrate that structural variations are entirely possible and potentially within the scope of the claims.

Exemplary embodiments of the invention have been described, but the invention is not limited to these embodiments. Various modifications may be made within the scope without departing from the subject matter of the invention read on the appended claims, the description of the invention, and the accompanying drawings.

What is claimed is:

1. A method of crimping a prosthetic valve, comprising:
providing a prosthetic valve crimping device having a plurality of rotationally constrained but radially movable jaws each having at least one camming member and a radially inner face such that the combination of all the radially inner faces defines a variable sized crimping aperture centered about a central axis, the crimping device further including an actuator connected to move a plurality of cams comprising spiral tracks each centered around the central axis that receive the jaw camming members;
positioning an expandable prosthetic valve within the crimping aperture, the prosthetic valve having an expanded diameter of at least 19 mm;
displacing the actuator such that the moving cams contact the at least one camming member on each jaw and apply radially inward forces to the jaws sufficient to narrow the crimping aperture and crimp the prosthetic valve down to a desired reduced diameter of at least 10 mm less than its expanded diameter; and
removing the crimped prosthetic valve from the crimping aperture and passing it through a prosthetic valve gauge attached to the prosthetic valve crimping device having a throughbore calibrated to the desired reduced diameter to ensure that the prosthetic valve has been crimped to the desired reduced diameter.

2. The method of claim 1, wherein the spiral tracks overlap one another.

3. The method of claim 2, wherein the actuator comprises a handle that rotates about the central axis, and the spiral tracks each extend around the central axis through an angle of at least 360°, and the method includes rotating the handle at least 270°.

4. The method of claim 1, wherein the actuator comprises a handle that rotates about the central axis, and the spiral tracks are formed on a rotatable camming plate, and the method comprises rotating the handle to rotate the camming plate.

5. The method of claim 1, wherein each jaw has at least two camming members extending on opposite sides of the jaw in axially opposite directions, wherein the plurality of cams comprises at least one cam on each axial side of the jaws, the method including applying radially inward forces with the at least one cam on each axial side of the jaws contacting the camming members on both sides of the jaws.

6. The method of claim 1, wherein the prosthetic valve comprises a prosthetic heart valve having an expanded diameter of between 19-29 mm, and wherein the method includes reducing the expanded prosthetic heart valve diameter by between about 14-24 mm.

7. The method of claim 1, wherein the prosthetic valve comprises a prosthetic heart valve having a balloon-expandable frame supporting a plurality of flexible leaflets within, the method including positioning the expanded prosthetic heart valve around a balloon on a balloon catheter prior to inserting the prosthetic heart valve into the crimping aperture and crimping the prosthetic heart valve over the balloon.

8. A method of crimping a prosthetic valve, comprising:
providing a disposable, portable crimping system for prosthetic valves, comprising a base, a valve crimper mounted on the base having a plurality of movable jaws defining a crimping aperture of variable diameter, and a prosthetic valve gauge mounted on the base having a tapered throughbore with a minimum diameter calibrated to be the same as a minimum diameter of the crimping aperture;
positioning an expandable prosthetic valve having an expanded diameter of at least 19 mm within the crimping aperture;
actuating the valve crimper jaws to narrow the crimping aperture and crimp the prosthetic valve down to the minimum diameter of at least 10 mm less than the expanded diameter; and
removing the crimped prosthetic valve from the crimping aperture and inserting it into the prosthetic valve gauge to ensure that the prosthetic valve has been crimped to the minimum reduced diameter.

9. The method of claim 8, wherein the prosthetic valve comprises a prosthetic heart valve having an expanded diameter of between 19-29 mm, and wherein the method includes reducing the prosthetic heart valve diameter by between about 14-24 mm.

10. The method of claim 9, wherein the prosthetic heart valve includes a balloon-expandable frame supporting a plurality of flexible leaflets within, the method including positioning the expanded prosthetic heart valve around a balloon on a balloon catheter prior to inserting the prosthetic heart valve into the crimping aperture and crimping the prosthetic heart valve over the balloon.

11. The method of claim 10, wherein the crimping system further includes a balloon gauge mounted on the base having a throughbore, and wherein prior to crimping the prosthetic heart valve the method includes expanding the balloon on the balloon catheter within the balloon gauge throughbore and calibrating the amount of inflation fluid necessary to inflate the balloon within the balloon gauge.

12. The method of claim 8, wherein the crimping system further includes a stop member removably mounted on the valve crimper so as to limit the minimum diameter of the crimping aperture.

13. The method of claim 8, wherein the movable jaws are radially movable relative to a central axis and each jaw has a radially inner face such that the combination of all the radially inner faces defines the variable diameter crimping aperture centered about the central axis, and wherein each jaw has at least one camming member and the valve crimper includes a rotating plate with spiral tracks each centered around the central axis that receive the jaw camming members, and the step of actuating the valve crimper jaws includes rotating the rotating plate to apply force with the spiral tracks to the jaw camming members.

14. The method of claim 8, wherein the movable jaws are radially movable relative to a central axis and each jaw has at least two camming members extending on opposite sides of the jaw in axially opposite directions, and the valve crimper includes two rotating plates, one on each axial side of the jaws, each plate having cam tracks each centered around the central axis which receive the jaw camming members, and the step of actuating the valve crimper jaws includes rotating the rotating plates to apply force with the cam tracks to the jaw camming members.

15. A method of crimping a prosthetic valve, comprising:
providing a prosthetic valve crimping device having a plurality of rotationally constrained but radially movable jaws each having at least one camming member and a radially inner face such that the combination of all the radially inner faces defines a variable sized crimping aperture centered about a central axis, the crimping device further including an actuator connected to move a plurality of cams;

positioning an expandable prosthetic valve within the crimping aperture, the prosthetic valve having an expanded diameter of at least 19 mm; and displacing the actuator such that the moving cams contact at least one camming member on each jaw and apply radially inward forces to the jaws sufficient to narrow the crimping aperture and crimp the prosthetic valve down to a reduced diameter of at least 10 mm less than its expanded diameter, wherein the prosthetic valve comprises a prosthetic heart valve having a balloon-expandable frame supporting a plurality of flexible leaflets within, the method including positioning the expanded prosthetic heart valve around a balloon on a balloon catheter prior to inserting the prosthetic heart valve into the crimping aperture and crimping the prosthetic heart valve over the balloon, and wherein prior to crimping the prosthetic heart valve the method includes expanding the balloon on the balloon catheter within a balloon gauge attached to the crimping device to calibrate the amount of inflation fluid necessary to inflate the balloon within the balloon gauge.

16. A method of crimping a prosthetic valve, comprising:
providing a prosthetic valve crimping device having a plurality of rotationally constrained but radially movable jaws each having at least one camming member and a radially inner face such that the combination of all the radially inner faces defines a variable sized crimping aperture centered about a central axis, the crimping device further including an actuator connected to move a plurality of cams;

positioning an expandable prosthetic valve within the crimping aperture, the prosthetic valve having an expanded diameter of at least 19 mm;

displacing the actuator such that the moving cams contact the at least one camming member on each jaw and apply radially inward forces to the jaws sufficient to narrow the crimping aperture and crimp the prosthetic valve down to a desired reduced diameter of at least 10 mm less than its expanded diameter; and removing the crimped valve from the crimping aperture and passing it through a prosthetic valve gauge attached to the prosthetic valve crimping device having a throughbore calibrated to the desired reduced diameter to ensure that the prosthetic valve has been crimped to the desired reduced diameter.

* * * * *